US006546288B1

(12) United States Patent
Levine

(10) Patent No.: US 6,546,288 B1
(45) Date of Patent: Apr. 8, 2003

(54) IMPLANTABLE CARDIAC STIMULATION SYSTEM WITH HIGH THRESHOLD RESPONSE AND PATIENT NOTIFICATION METHOD

(75) Inventor: Paul A. Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/884,697

(22) Filed: Jun. 18, 2001

(51) Int. Cl.[7] .............................................. A61N 1/362
(52) U.S. Cl. ....................................................... 607/28
(58) Field of Search ................................ 607/9, 27, 28

(56) References Cited

U.S. PATENT DOCUMENTS

| 4,130,131 A | 12/1978 | Kucenty ................. 137/512.1 |
| 4,140,131 A | 2/1979 | Dutcher et al. ........ 128/419 PT |
| 4,407,288 A | 10/1983 | Langer et al. ......... 128/419 PG |
| 4,686,988 A | 8/1987 | Sholder ................ 128/419 PT |
| 4,708,142 A | 11/1987 | DeCote, Jr. ........... 128/419 PT |
| 4,729,376 A | 3/1988 | DeCote, Jr. ........... 128/419 PT |
| 4,969,467 A | 11/1990 | Callaghan et al. ..... 128/419 PG |
| 5,003,975 A | * 4/1991 | Hafelfinger et al. |
| 5,076,272 A | 12/1991 | Ferek-Petric .......... 128/419 PG |
| 5,350,410 A | 9/1994 | Kleks et al. ................... 607/28 |
| 5,476,485 A | * 12/1995 | Weinberg et al. |
| 5,549,653 A | 8/1996 | Stotts et al. ..................... 607/4 |
| 5,607,459 A | 3/1997 | Paul et al. ..................... 607/29 |
| 5,609,614 A | 3/1997 | Stotts et al. ................... 607/29 |
| 5,609,615 A | 3/1997 | Sanders et al. ............... 607/36 |
| 5,628,776 A | 5/1997 | Paul et al. .................... 607/119 |
| 5,630,838 A | 5/1997 | Prutchi et al. .............. 607/116 |
| 5,643,328 A | 7/1997 | Cooke et al. ................. 607/36 |
| 5,709,712 A | 1/1998 | Paul et al. ..................... 607/27 |
| 5,755,742 A | 5/1998 | Schuelke et al. ............. 607/27 |
| 5,846,264 A | 12/1998 | Andersson et al. ........... 607/28 |
| 6,067,473 A | 5/2000 | Greeninger et al. ......... 607/32 |

* cited by examiner

Primary Examiner—Scott M. Getzow

(57) ABSTRACT

An implantable cardiac stimulation device and associated method provide automatic capture verification and threshold testing capabilities with an added high-threshold response algorithm and patient notification process. The stimulation device responds to higher than normal capture thresholds by permitting the stimulation pulse energy to be set above the fixed maximum pulse energy normally allowed by automatic capture verification techniques. In order to maintain comfortable yet effective stimulation, the high-energy stimulation is delivered in a bipolar configuration. The stimulation device alerts the patient of the change to high-energy output when it occurs. After the high-energy output is automatically set, one or more high-energy stimulation pulses are delivered in a unipolar configuration on a scheduled or event-triggered basis. A unipolar high-energy stimulation pulse is typically perceptible by the patient due to stimulation of excitable tissue surrounding the device housing. Sensation of a periodic high-energy pulse alerts the patient that stimulation conditions have changed and medical attention should be sought.

49 Claims, 7 Drawing Sheets

IMPLANTABLE CARDIAC STIMULATION SYSTEM WITH HIGH THRESHOLD RESPONSE AND PATIENT NOTIFICATION METHOD

FIELD OF THE INVENTION

The present invention is directed to implantable cardiac electrical stimulation devices. More specifically, the present invention is directed to a cardiac electrical stimulation device possessing automatic capture with a high threshold response and patient notification method.

BACKGROUND OF THE INVENTION

In the normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (A-V) node and a ventricular conduction system causing a depolarization known as an R-wave and the resulting ventricular chamber contractions.

Disruption of this natural pacing and conduction system as a result of aging or disease can be successfully treated by artificial cardiac pacing using implantable cardiac stimulation devices, including pacemakers and implantable defibrillators, which deliver rhythmic electrical pulses or anti-arrhythmia therapies to the heart at a desired energy and rate. A cardiac stimulation device is electrically coupled to the heart by one or more leads possessing one or more electrodes in contact with the heart muscle tissue (myocardium). One or more heart chambers may be electrically stimulated depending on the location and severity of the conduction disorder.

A stimulation pulse delivered to the myocardium must be of sufficient energy to depolarize the tissue, thereby causing a contraction, a condition commonly known as "capture." In early pacemakers, a fixed, high-energy pacing pulse was delivered to ensure capture. While this approach is straightforward, it quickly depletes battery energy and can result in patient discomfort due to extraneous stimulation of surrounding skeletal muscle tissue.

The capture "threshold" is defined as the lowest stimulation pulse energy at which capture occurs. By stimulating the heart chambers at or just above threshold, comfortable and effective cardiac stimulation is provided without unnecessary depletion of battery energy. Threshold, however, is extremely variable from patient-to-patient due to variations in electrode systems used, electrode positioning, physiological and anatomical variations of the heart itself, and so on. Furthermore, threshold will vary over time within a patient as, for example, fibrotic encapsulation of the electrode occurs during the first few weeks after surgery. Fluctuations may even occur over the course of a day or with changes in medical therapy or disease state.

Modern pacemakers have incorporated techniques for monitoring the cardiac activity following delivery of a stimulation pulse in order to verify that capture has indeed occurred. If a loss of capture is detected by such "capture-verification" algorithms, a threshold test is performed by the cardiac pacing device in order to re-determine the threshold and automatically adjust the stimulating pulse energy. This approach, called "automatic capture" improves the cardiac stimulation device performance in at least two ways: 1) by verifying that the stimulation pulse delivered to the patient's heart has been effective, and 2) greatly increasing the device's battery longevity by conserving the energy used to generate stimulation pulses.

Commonly implemented techniques for verifying capture involve monitoring the internal myocardial electrogram (EGM) signals received on the implanted cardiac electrodes. When a stimulation pulse is delivered to the heart, the EGM signals that are manifest concurrent with depolarization of the myocardium are examined. When capture occurs, an "evoked," which is the intracardiac P-wave of R-wave that indicates depolarization of the respective cardiac tissue, may be detected. The depolarization of the heart tissue in response to the heart's natural pacing function is referred to as "intrinsic response". Through sampling and signal processing algorithms, the presence of an evoked response following a stimulation pulse is determined. For example, if a stimulation pulse is applied to the ventricle, an R-wave sensed by ventricular sensing circuits of the pacemaker immediately following application of the ventricular stimulation pulse evidences capture of the ventricles. If no evoked response is detected, typically a higher-energy, back-up stimulation pulse is delivered to the heart very shortly after the primary ineffective stimulus, commonly in the order of 60–100 ms, in order to maintain the desired heart rate.

The output of the primary pulse is then progressively increased to restore stable capture. This is followed by an automatic threshold test to determine the minimum pulse required to capture the heart at that time. Threshold tests may also be performed on a periodic basis, for example three times a day, daily or weekly. An exemplary automatic threshold determination procedure is performed by first increasing the stimulation pulse output level to a relatively high predetermined testing level at which capture is certain to occur. Thereafter, the output level is progressively decremented until capture is lost after which the output is progressively increased in small steps until capture is reestablished. The stimulation pulse energy is then set to a level above the lowest output level at which capture was attained. This additional working margin above the measured threshold allows for small fluctuations in threshold to occur without risk of loss of capture and frequent delivery of both back-up pulses and initiation of the threshold testing sequence. A safety margin for the patient is provided by a fixed significantly higher output of the back-up pulse. Thus, reliable capture verification is of utmost importance in proper determination of the threshold.

Such automatic methods for verifying and maintaining capture are currently implemented in cardiac stimulation devices utilizing bipolar sensing and unipolar stimulation. In commercially available cardiac pacing devices with automatic capture verification capabilities, a fixed maximum stimulation pulse energy is set, at which the autocapture feature becomes disabled. The advantage of setting a maximum stimulation pulse energy limit is to minimize patient discomfort should the output be increased to the maximum allowed setting in the situation of rising thresholds. This maximum value is higher than the default output value for most pacemakers recently introduced to the market.

Automatic capture routines thus improve pacemaker performance as long as the capture threshold remains within a normal range of stimulation pulse energies. However, if a pacing-dependent patient undergoes an unexpected, massive increase in threshold, for example if an electrode shifts acutely or the threshold rises on a chronic basis due to progression of disease or as a side-effect of a new pharmacologic agent, the fixed maximum stimulation pulse energy allowed by Autocapture may not effectively capture the heart. Therefore, in these cases, further increases in pulse energy may be needed.

Allowance of high-energy output will afford the patient greater protection against ineffective stimulation. Therefore, it would be desirable to allow exceptional conditions to supercede the present autocapture maximum output limit. With automatic capture enabled, the frequency of follow-up evaluations may have been reduced, but the patient will be protected by the automatic capture algorithm in the presence of a rising capture threshold.

However, a rising output energy requirement could deplete the pacemaker battery energy more quickly than under normal stimulation conditions resulting in device failure prior to the next scheduled follow-up evaluation. Notifying the patient that a change in stimulation conditions has occurred that warrants medical evaluation would therefore be important to not only prevent unexpected battery depletion but allow further evaluation as to the reasons for the significant rise in the capture threshold.

Patient warning systems have been proposed to alert patients of conditions that warrant medical attention such as a detected lead failure, impending battery depletion, or loss of capture. Reference is made to U.S. Pat. No. 5,076,272 to Ferek-Petric and U.S. Pat. No. 4,140,131 to Dutcher et al. In typical patient warning systems, detection circuitry for identifying conditions that warrant patient notification or warning are included, such as lead impedance measurements for detection of lead failure or battery voltage level detectors. Not addressed heretofore is the recognition of an appropriate increase in stimulation output in response to a large increase in capture threshold, which may accelerate battery depletion or signal either a potential problem with the pacing lead or a change in the patient's clinical status that would warrant further evaluation.

Typical patient warning systems involve additional hardware or circuitry. Additional electrodes or conductive elements implanted away from the heart have been proposed to provide muscle stimulation (or nerve stimulation) to alert a patient of a condition that warrants medical attention. Reference is made to the U.S. Pat. No. 5,076,272 to Ferek-Petric; U.S. Pat. No. 4,140,131 to Dutcher et al. supra; U.S. Pat. No. 5,549,653 to Stotts et al.; U.S. Pat. No. 5,609,615 to Sanders; and U.S. Pat. No. 5,643,328 to Cooke et al.

With additional dedicated electrodes or conductive elements for patient warning stimulation, dedicated output circuitry is required to deliver stimulation pulses to the patient warning element, or additional circuitry is required to divert stimulation output from standard heart leads to the patient warning element. Implementation methods for delivering stimulation to an auxiliary stimulation element for patient warning is described U.S. Pat. No. 5,076,272 to Ferek-Petric; U.S. Pat. No. 4,140,131 to Dutcher et al. supra. Reference is also made to U.S. Pat. No. 5,709,712 to Paul et al., and U.S. Pat. No. 4,407,288 to Langer et al. Another approach for delivering patient warning stimulation is the use of one output channel of a dual chamber cardiac stimulation device. By placing a pin electrode in one output channel, stimulation of the local tissue can be achieved, however, the dual chamber stimulation device is functionally reduced to a single chamber stimulation device. Reference is made to U.S. Pat. No. 5,549,653 to Stotts et al.

It would therefore be desirable to provide, in a cardiac stimulation device possessing automatic capture verification and maintenance methods, a method for responding to a high increase in capture threshold in order to provide further assurance of effective stimulation therapy. In case high-energy stimulation is required, it would also be desirable to provide a method for notifying the patient that a change in stimulation conditions has occurred and medical attention should be sought. It would be further desirable to provide a patient warning system without requiring additional circuitry or hardware or otherwise limiting the cardiac stimulation device functionality.

SUMMARY OF THE INVENTION

The present invention addresses these needs by providing a stimulation device and method for providing automatic capture verification and threshold testing capabilities with an added high-threshold response algorithm and patient notification method. To this end, the stimulation device responds to higher than normal capture thresholds by permitting the stimulation pulse energy to be set above the fixed maximum pulse energy normally allowed by automatic capture verification techniques.

One object of the present invention is to provide a high threshold response algorithm that sets the pulse energy to the maximum device output after repeated automatic threshold tests result in the identification of a high threshold. In an alternative embodiment, the pulse energy may be incremented in a step-wise fashion, above the maximum pulse energy normally allowed by an automatic capture verification routine. In this embodiment, periodic threshold tests are repeated to ensure the incremented pulse energy remains above threshold. In order to maintain comfortable yet effective stimulation, the high-energy stimulation is delivered in a bipolar configuration, rather than unipolar, to avoid patient discomfort. Automatic capture detection that normally requires unipolar stimulation is disabled.

Another object of the present invention is to alert the patient of the change to high-energy output when it occurs. After the high-energy output is automatically set, one or more high-energy stimulation pulses are delivered in a unipolar configuration on a scheduled or event-triggered basis. A unipolar high-energy stimulation pulse is typically perceptible by the patient due to stimulation of excitable tissue surrounding the device housing. Sensation of a periodic high-energy pulse alerts the patient that stimulation conditions have changed and medical attention should be sought.

Thus, one feature of the present invention is a method that responds to a large increase in capture threshold by automatically setting a high-energy stimulation pulse output. Another feature of the present invention is the ability to switch stimulation electrode configuration from unipolar to bipolar stimulation when the high-energy output is set in response to a high threshold. Yet a further feature of the present invention is a method for notifying the patient that a significant change in stimulation condition has occurred.

The foregoing and other objects and features of the present invention are realized by providing an implantable stimulation device equipped with cardiac data acquisition capabilities. A preferred embodiment of the stimulation device includes a control system for controlling the operation of the device and executing various test algorithms such as capture verification and threshold testing; a set of leads for receiving cardiac signals and for delivering atrial and ventricular stimulation pulses; switching circuitry to allow switchable selection of sensing and stimulation electrode configurations; a set of sensing circuits comprised of sense amplifiers for sensing and amplifying the cardiac signals; and pulse generators for generating atrial and ventricular stimulation pulses. In addition, the device includes memory for storing operational parameters used by the control system. The device also includes a telemetry circuit for communicating with an external device.

When operating according to a preferred embodiment, the control system performs a threshold search whenever a sustained loss of capture is detected, e.g. loss of capture on at least two consecutive cycles, according to known automatic capture techniques. If the threshold test results for two consecutive threshold tests indicate a large increase in threshold, automatic capture is disabled by the control system and the stimulation pulse energy is reset to the highest available output. Alternatively, the pulse energy is increased in a step-wise fashion. The electrode configuration is switched to bipolar by switching circuitry under control of the control system. A patient notification to the changed stimulation conditions is delivered by switching the electrode configuration back to unipolar for one or more stimulation pulses after which bipolar stimulation is again resumed. The patient notification may occur at a scheduled time of day, or upon a pre-defined event such as a given number of stimulation pulses or stimulation at the programmed rest rate.

In an alternative embodiment, a tiered response to rising capture threshold is provided. The stimulation output is adjusted to a level equal to the capture threshold plus a working margin whenever a threshold test is performed. The working margin applied depends on the range of output settings in which the capture threshold falls. For relatively low capture thresholds, a normal working margin is applied. For relatively high capture thresholds a larger working margin is applied. If the stimulation output exceeds a predefined alarm level, the patient notification system is enabled.

In another embodiment, the high threshold response includes lead surveillance. Lead impedance measurements are made to determine if lead failure is the likely cause of the large increase in capture threshold. If so, the high output stimulation is delivered using a unipolar electrode stimulation configuration to eliminate the use of the defective lead.

The system and method of the present invention thus provide an appropriate response to a massive rise in capture threshold by allowing the stimulation pulse energy to be set to a high output as necessary to maintain effective stimulation therapy. The present invention further provides a patient warning system to alert the patient of this change in stimulation conditions so that medical attention may be sought. The rise in threshold may indicate a change in clinical condition that warrants medical attention. The increased output will drain battery energy more quickly than anticipated. By making a clinician aware of the altered stimulation conditions, patient follow-up can be scheduled as needed. The present invention thus improves stimulation device performance by ensuring safe and effective stimulation therapy even under high threshold conditions without risking unexpected battery depletion.

BRIEF DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items, and wherein:

DETAILED DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

As indicated above, it is an object of the present invention to provide a safe and appropriate response to a large increase in capture threshold. The methods provided in the present invention, as will be described in detail in conjunction with FIGS. 3 through 6, may be included in a single chamber, dual chamber, or multichamber cardiac stimulation device having pacing, cardioversion, and defibrillation capabilities. One such cardiac stimulation device will now be described in conjunction with FIGS. 1 and 2.

Figure 1:
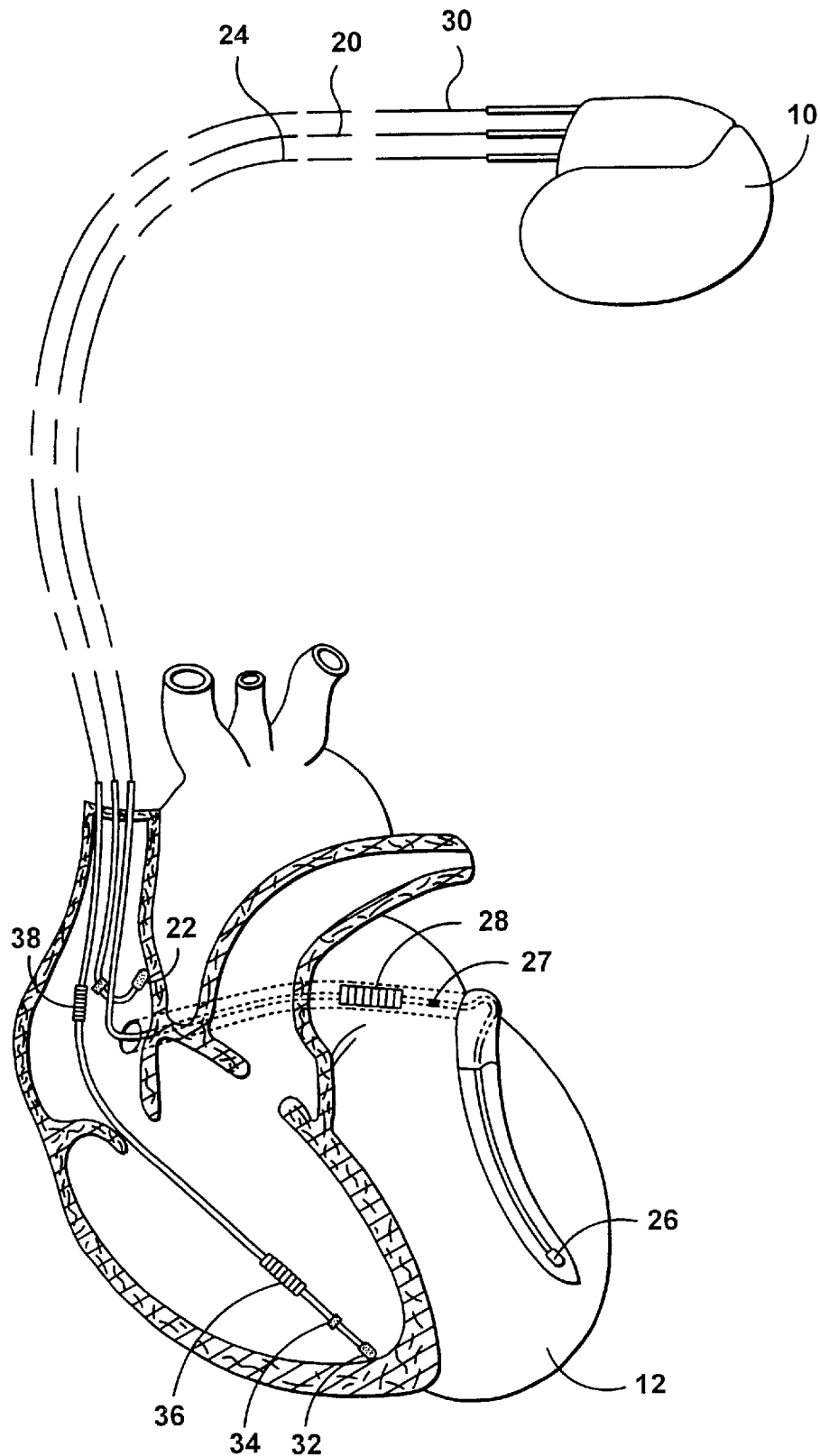
FIG. 1 is a simplified diagram illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
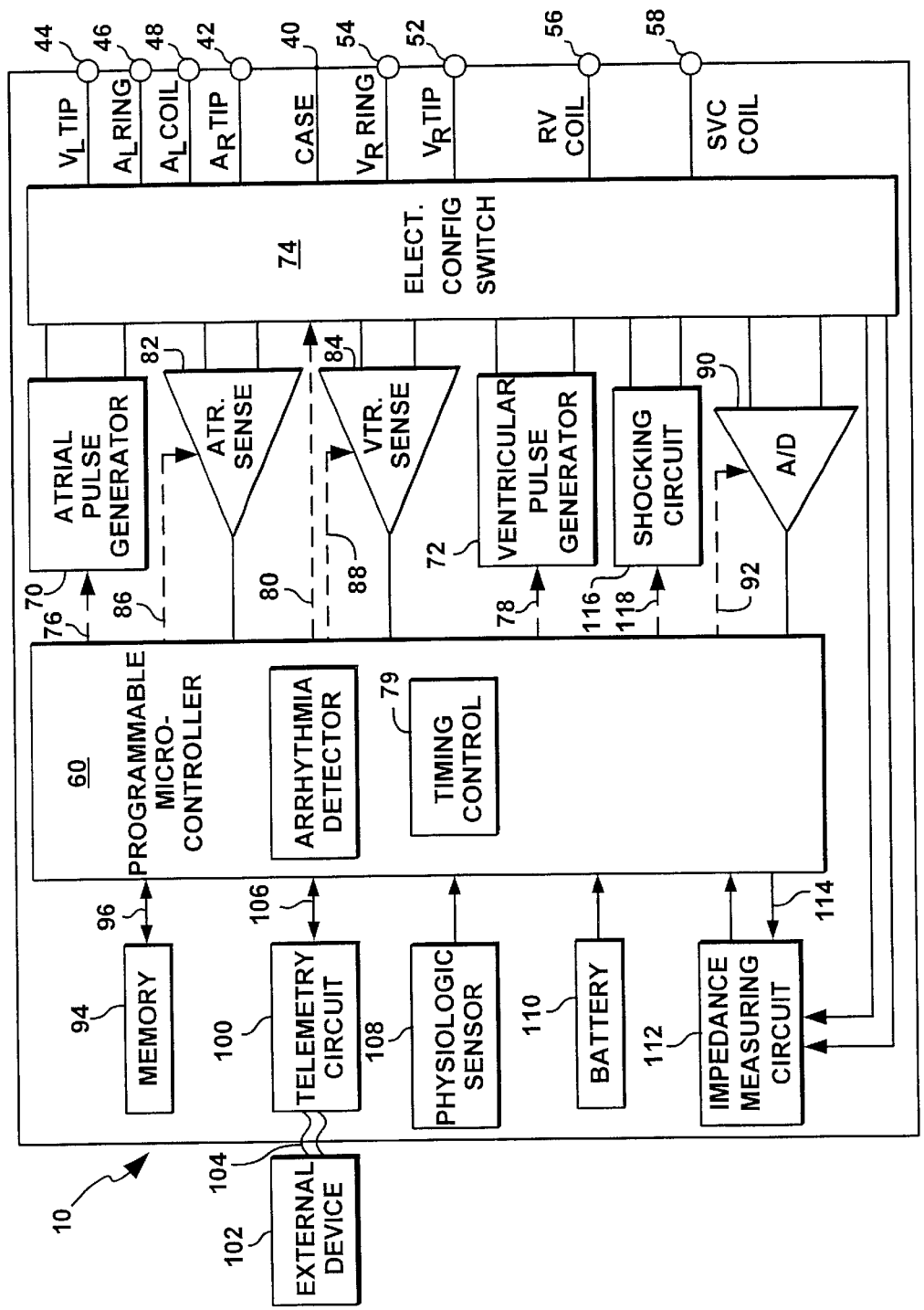
FIG. 2 is a functional block diagram of a multi-chamber implantable stimulation device illustrating the basic elements of a stimulation device that can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. The microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. Any suitable microcontroller 60 may be used carry out the functions described herein.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, cross-chamber, etc.) by selectively closing the appropriate combination of switches.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller, or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the atrial or ventricular pulse generators, 70 or 72, to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

Capture detection may occur on a beat-by-beat basis or on a sampled basis. Preferably, a capture threshold search is performed once a day during at least the acute phase (e.g., the first 30 days) and less frequently thereafter. A capture threshold search would begin at a desired starting point (either a high energy level or the level at which capture is currently occurring) and decrease the energy level until capture is lost. The lowest level at which capture occurs is known as the capture threshold. Thereafter, a safety margin is added to the capture threshold.

The implementation of capture detection circuitry and algorithms are described, for example, in U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et al.); and U.S. Pat. No. 5,350,410 (Mann et al.), which patents are hereby incorporated herein by reference. The type of capture detection system used is not critical to the present invention.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

The operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

As further shown in FIG. 2, the device 10 is shown as having an impedance measuring circuit 112 which is enabled by the microcontroller 60 via a control signal 114. The known uses for an impedance measuring circuit 120 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
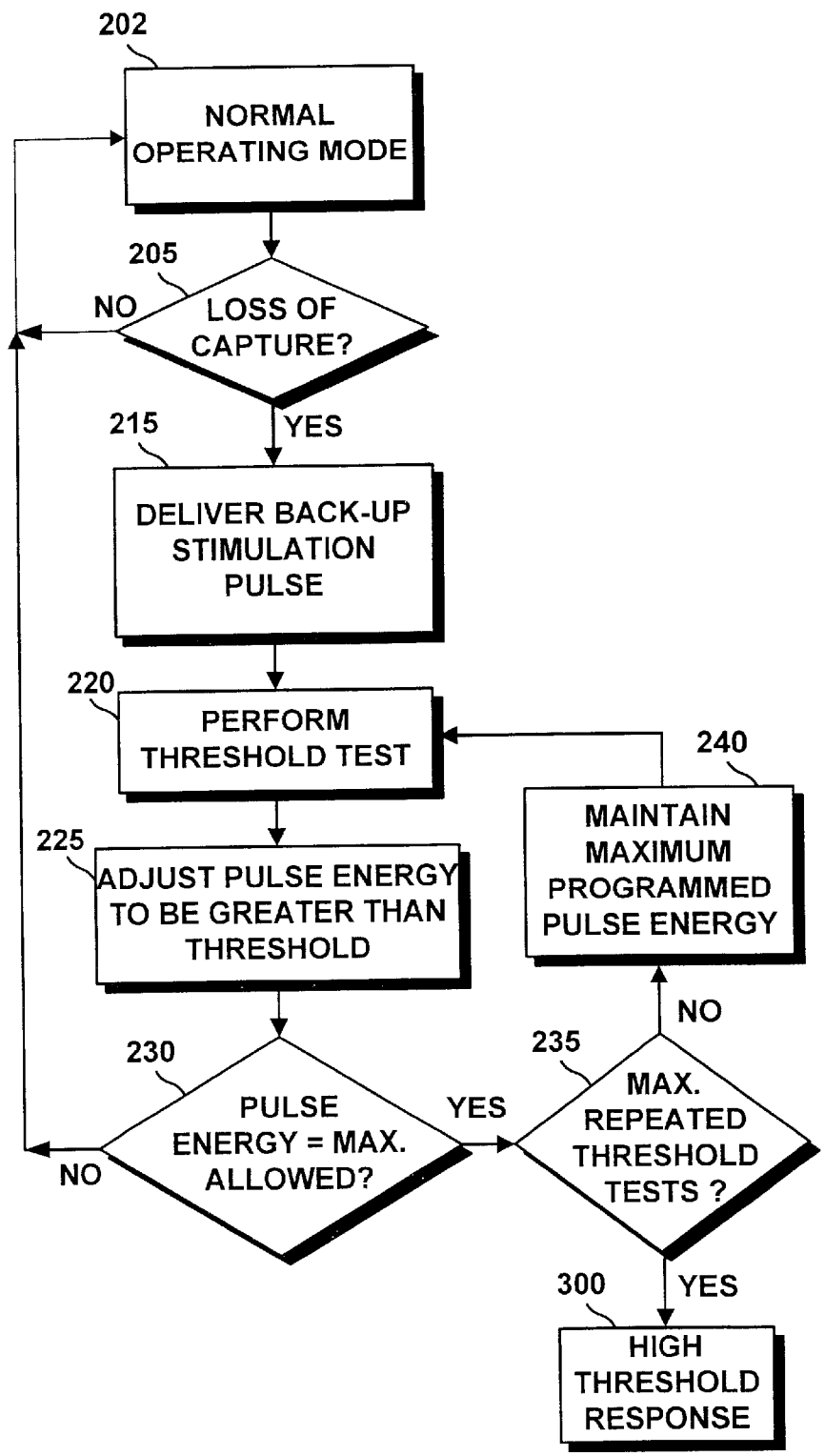
FIG. 3 is a flow chart describing an overview of the operation of one embodiment of the present invention for triggering a high threshold response method.

In FIG. 3, a flow chart is shown describing an overview of the operation and novel features implemented in one embodiment of the device 10. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

FIG. 3 is a flow chart describing a method 200 for triggering a high threshold response. Block 202 of method 200 represents the normal operating mode of device 10 in which intrinsic cardiac activity is sensed and stimulation therapy is delivered according to the programmed operating parameters. During this operating mode, automatic capture can be enabled so that whenever a pacing or stimulation pulse is delivered, verification of an evoked response is made. As long as capture is verified, as determined at decision step 205, the device 10 continues to operate in the normal mode 202.

If, however, at decision step 205, the automatic capture feature detects a loss of capture, a back-up stimulation pulse will be delivered at step 215. The back-up stimulation pulse is typically delivered at a predefined safety interval above the programmed pulse energy. The back-up stimulation pulse energy may be progressively increased until capture is regained.

Once capture is regained, a threshold test is performed at step 220 in order to measure the capture threshold at the present time. The programmed pulse energy is then automatically adjusted at step 225 to a setting equal to the measured threshold plus a working margin that allows for small fluctuations in threshold.

Steps 205 through 225 represent a sequence of operations included in an exemplary automatic capture method, it being understood that alternative automatic capture methods may be used. At decision step 230, microprocessor 60 determines if the new pulse energy setting is equal to the maximum pulse energy setting allowed during automatic capture. The maximum pulse energy allowed during automatic capture is typically not the maximum pulse energy available from the device 10.

For example, the maximum allowed pulse energy when automatic capture is enabled may be an amplitude of 4.5 Volts while the device 10 may be capable of delivering a pulse 7.5 Volts in amplitude. If the adjusted pulse energy is not equal to the maximum energy allowed during automatic capture, the device 10 may return to the normal operating mode 202 with the automatic capture still enabled.

If the pulse energy has reached the maximum allowed during automatic capture, as determined at decision step 230, and this maximum setting is the result of a predefined number of repeated threshold tests (decision step 235), for example 2 or more threshold tests, then a high threshold response method 300 is called upon. The high threshold response method 300 will be described in detail in conjunction with FIG. 4.

The number of threshold tests resulting in the maximum allowable pulse energy that are required before initiating the high threshold response method 300 is preferably a programmable number. Fusion or pseudofusion events, or other causes, may lead to a false loss of capture detection. Before responding to a high threshold result, the threshold test is preferably repeated to verify an actual rise in threshold. If the desired number of repeated threshold tests has not been reached at decision step 235, then the maximum pulse energy setting will be maintained for a given number of cardiac cycles at step 240, after which a threshold test 220 will be repeated.

Figure 4:
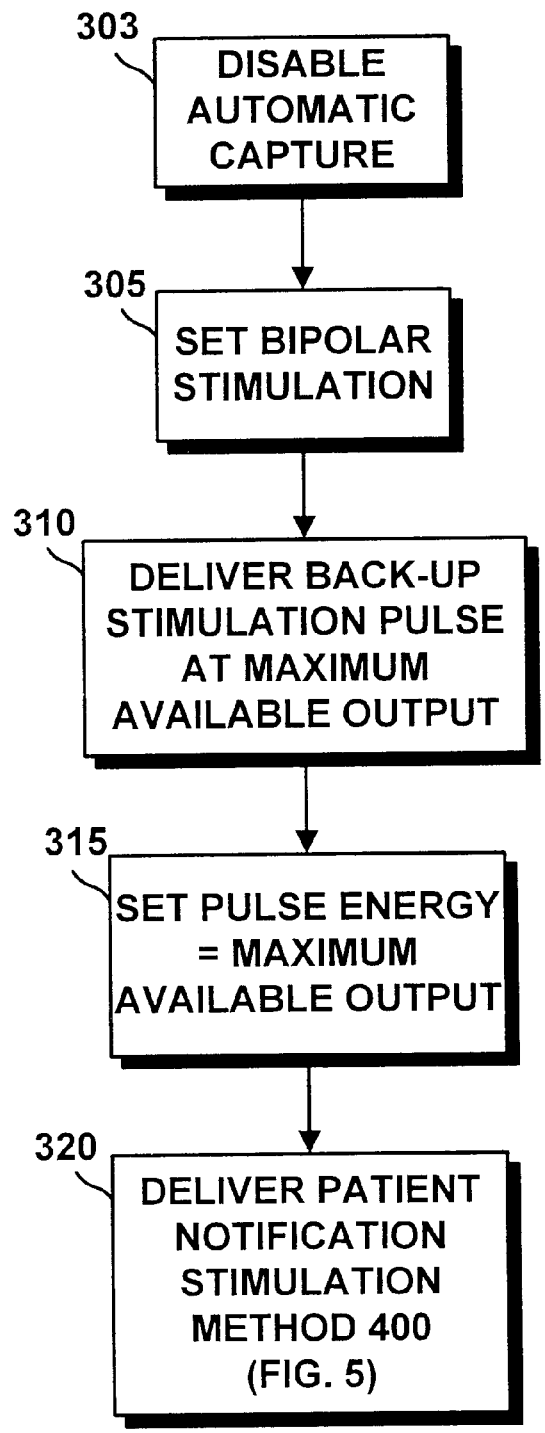
FIG. 4 is a flow chart describing the operation of one embodiment of a high threshold response method according to the present invention.

As shown in FIG. 4, the high threshold response algorithm 300 begins at step 303 by disabling the automatic capture feature. At step 305 the stimulation electrode configuration is set to a bipolar combination. This is accomplished through switch 74, which selectively connects an appropriate bipolar pair of electrodes for stimulating the heart chamber in which the high threshold has been measured.

At step 310, a back-up stimulation pulse is delivered at the maximum output available from the device 10, for example 7.5 Volts amplitude and 1.0 msec pulse width. By setting the stimulation electrode configuration to bipolar at the previous step 305, patient discomfort caused by the high energy output setting is minimized. The automatic capture has been disabled (step 303) prior to this bipolar high energy output because automatic capture methods normally require bipolar sensing during unipolar stimulation for accurate evoked response detection. Until such time that automatic capture methods are available that can be utilized with bipolar stimulation, the automatic capture feature is disabled during the high threshold response method 300.

At step 315, the pulse energy is set to remain at the maximum available pulse energy during the normal operation 202 of device 10. At step 320, a patient notification method 400 is initiated to alert the patient that a change in stimulation condition has occurred, as it will be described in connection with FIG. 5.

Figure 5:
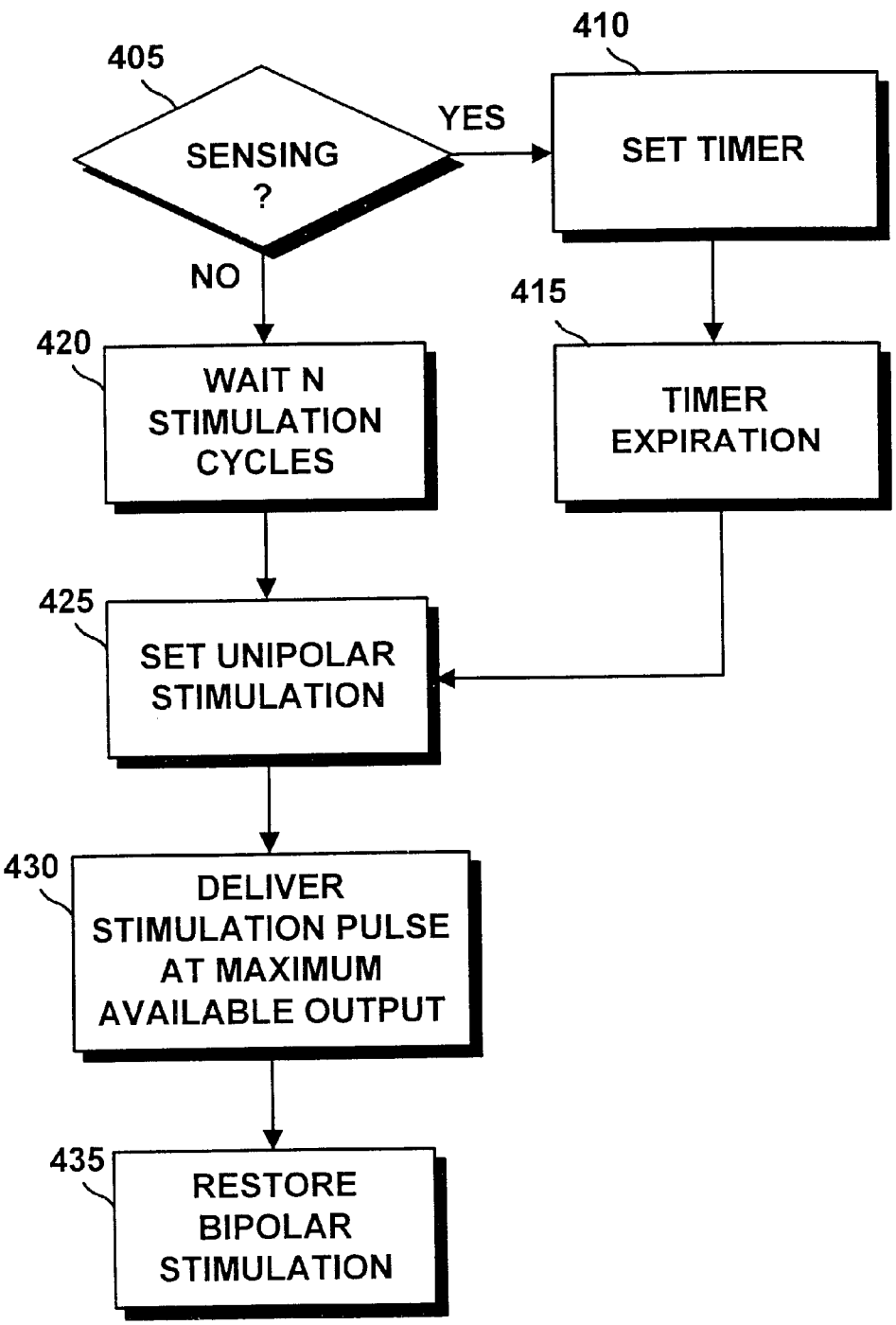
FIG. 5 is a flow chart describing the operation of a patient notification method included in one embodiment of the present invention.

As shown in FIG. 5, the patient notification method 400 begins by first determining if the device 10 is presently sensing or stimulating at decision step 405. If device 10 is stimulating, the stimulation electrode configuration is switched from bipolar back to unipolar (step 425) after a predetermined number (N) of stimulation cycles (step 420).

Thus, at step 430, the next stimulation pulse is delivered as a unipolar pulse. This high-energy unipolar stimulation pulse is expected to be perceptible by the patient. The perception of the stimulation pulse notifies the patient that the stimulation condition has changed and the patient has been advised to seek medical attention when such a situation arises. At step 430, a unipolar stimulation pulse may be delivered for one or more consecutive stimulation cycles.

After the desired number of notification pulses have been delivered, the bipolar electrode configuration is restored at step 435. The patient notification method may then be repeated by returning to step 405 and delivering additional notification pulses after the predetermined number of stimulation cycles.

If the device 10 is predominately sensing rather than stimulating at decision step 405, a timer may be used to trigger the delivery of notification pulses rather than a number or cycles. A timer is set at step 410, and upon expiration of the timer at step 415, the stimulation electrode configuration is set to unipolar at step 425. Unipolar stimulation pulses are delivered in a triggered mode at step 430 to notify the patient of the changed stimulation conditions. The number of triggered stimulation pulses is preferably programmable. The triggered stimulation pulse may be delivered coincidentally with the next sensed event or may be delivered a given time interval relative to the next sensed event.

In alternative embodiments, one or more unipolar notification pulses may be delivered at programmed intervals of time such as hourly, daily or weekly. Such timed notification pulses may be substituted for a demand stimulation pulse or be delivered in a triggered mode based on a sensed event. In either case the notification pulse is still delivered in a cardiac synchronous manner. One or more unipolar notification pulses may also be delivered at a programmed time of day, selectable by the physician. In yet another embodiment, one or more unipolar notification pulses may be delivered at a time identified by a specific operating behavior of device 10. For example, when the device 10 is functioning at the base rate, at the rest rate, or another selected operating behavior. It is recognized that numerous algorithms may be used to trigger the delivery of notification pulses which may be successfully implemented in the present invention without deviating from the goal of the present invention.

Delivery of the unipolar notification pulses alerts the patient to a change in stimulation condition for which medical attention should be sought. This notification in turn alerts the clinician state so that the cause of the high threshold state may be investigated. The high threshold state may reflect a change in the cardiac status, a mechanical problem developing with the lead or an adverse effect from a concomitant medical condition or pharmacological agent.

If the threshold has increased and the patient is otherwise stable, the high output condition may be maintained but, knowing that this may result in accelerated battery depletion, the clinician can schedule more frequent follow-up visits. Furthermore, in choosing to maintain the high output condition, the clinician can program the patient notification method to be disabled so that the patient does not continue to experience sensation associated with unipolar notification pulses.

Figure 6:
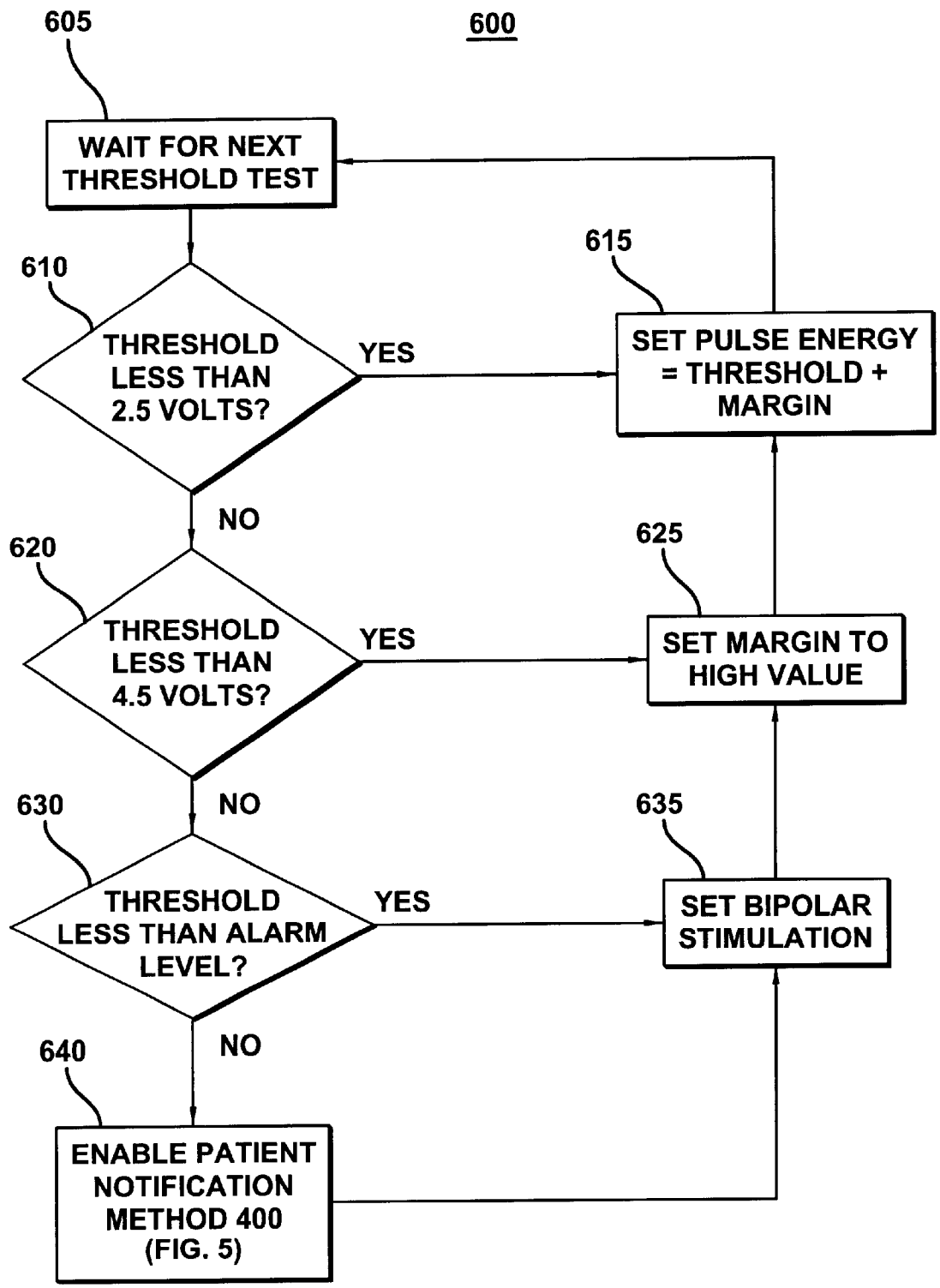
FIG. 6 is a flow chart describing the operation of a high threshold response method included in an alternative embodiment of the present invention that provides a tiered response to rising threshold.

FIG. 6 illustrates a flow chart that depicts an alternative method 600 for the high threshold response feature previously described and illustrated in FIG. 4. Normally, after a threshold test, the pulse energy is set a working margin above the measured threshold to allow for small fluctuations in threshold without the risk of frequent loss of capture, backup pulse delivery and repeated threshold tests. This working margin is typically on the order of 0.25 Volts, which is adequate when threshold remains at relatively low, normal levels. However, as threshold increases, the working margin may need to be increased. Threshold fluctuation is more likely to be within a given percentage of the threshold rather than within a fixed narrow margin, like 0.25 Volts. Therefore, as threshold increases, a higher working margin is desirable.

In FIG. 6, a tiered response to rising threshold is illustrated that allows an increased working margin to be applied as threshold increases. At step 605 of method 600, the tiered response method waits for a threshold test to be performed as a result of loss of capture or as a periodic threshold search. If the measured threshold at step 605 is below a predefined level, for example 2.5 Volts, as determined at decision step 610, the working margin remains at the normal setting, typically 0.25 Volts. The pulse energy is adjusted to the new threshold plus the working margin at step 615.

If the threshold rises above the predefined level (in this example 2.5 Volts), but remains below the maximum allowed setting for automatic capture (commonly 4.5 Volts), as determined at decision step 620, the working margin is increased to a higher value, for example 0.5 Volts, at step 625. Thus if threshold remains below 2.5 Volts, for example 2.0 Volts, a working margin of 0.25 Volts is used such that the stimulation pulse energy would be set to 2.25 Volts. If the threshold increases to 3.0 Volts, the higher working margin of 0.5 Volts is used such that the stimulation pulse energy set at step 615 would be 3.5 Volts.

If the threshold continues to rise such that the stimulation pulse energy reaches or exceeds the maximum allowed during automatic capture (commonly 4.5 Volts) but remains below a predefined alarm level (decision step 630), the tiered response algorithm allows the pulse energy to be adjusted to the higher setting. First, the electrode configuration is switched to bipolar at step 635, the working margin is kept at the higher setting at step 625, and the pulse energy is set equal to the measured threshold plus the higher working margin. Bipolar stimulation prevents patient discomfort at the higher pulse energy setting. Automatic capture remains enabled to track the rising threshold.

In another embodiment, the automatic capture feature remains enabled with bipolar output. Alternatively, the mode reverts to a unipolar output configuration starting at the very high output, which will allow for continued monitoring of the capture threshold. This feature can be incorporated in the patient notification system.

In another embodiment, if the capture threshold reaches a second predetermined level (e.g. 6.5 Volts), such that the maximum allowed output does not provide an adequate safety margin, the stimulation device 10 reverts to a maximal output but remains in the unipolar output configuration. This embodiment is likely to be used in a relative emergency situation.

In another embodiment, if the capture threshold reaches a second predetermined level (e.g. 6.5 Volts), such that the maximum allowed output does not provide an adequate safety margin, the stimulation device 10 reverts to a maximal output but remains in the unipolar output configuration. If, based on previous testing, this output has been demonstrated to not induce local muscle stimulation, the notification system will allow an even higher output to be programmed for the notification pulses (e.g. 10 Volts) and these will be delivered on a periodic basis consistent with the earlier described notification systems.

If the threshold rises even further, exceeding a predefined alarm level as determined at decision step 630, the patient notification method 400 is executed at step 640, as previously described and illustrated in FIG. 5. The alarm level may be the maximum available output, for example 7.5 Volts or a lower setting as selected by a clinician. After delivering the unipolar notification pulses, bipolar stimulation at the high output setting continues. Automatic capture remains enabled.

Figure 7:
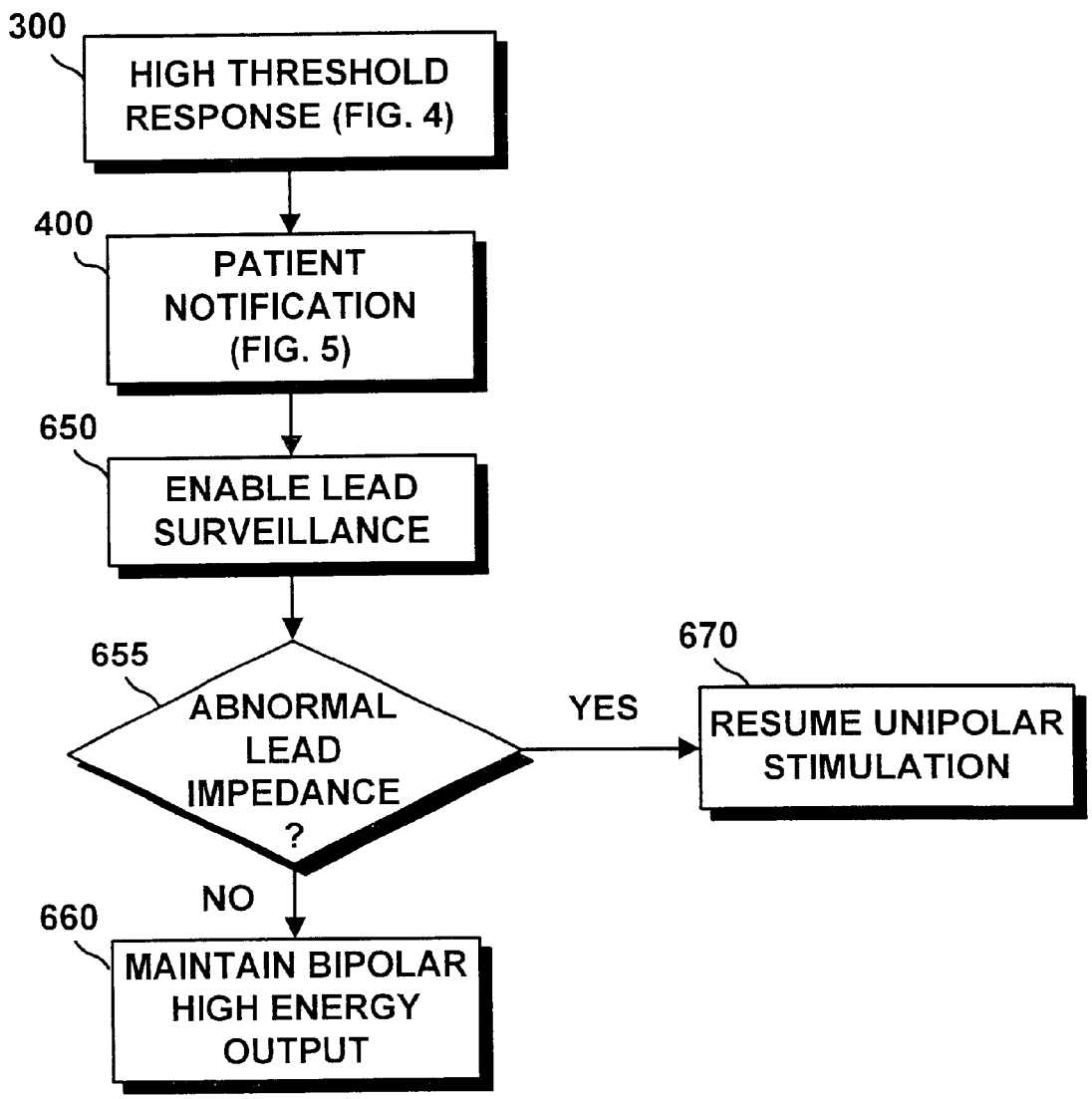
FIG. 7 is a flow chart describing the operation of an alternative embodiment of the high threshold response method that includes lead surveillance.

One cause for a massive rise in threshold is lead failure. Lead dislodgment may cause an increase in capture threshold. A lead fracture or a breach of the internal insulation can also cause an increase in threshold and will preclude effective delivery of bipolar stimulation to the heart. Therefore, an added feature of lead surveillance is included in one embodiment of the high threshold response 300. In FIG. 7, an alternative method 700 for high threshold response is illustrated that includes lead surveillance.

Block 300 of FIG. 7 represents the high threshold response as previously described in conjunction with FIG. 4. Block 400 represents the patient notification method as previously described in conjunction with FIG. 4. Once these methods have been activated, a lead surveillance method is also enabled at step 650. Any suitable method of monitoring lead integrity, such as known lead impedance measurement techniques, may be used in the lead surveillance method, in order to determine if lead failure is suspected to be the cause of the high threshold.

If abnormal lead impedance is measure, either very high or very low, as determined at decision step 655, the stimulation electrode configuration is returned to unipolar at step 670. The high output setting is maintained. Bipolar stimulation, as called for by the high threshold response 300, will be ineffective if a lead has failed.

Therefore, to preserve effective pacing therapy, the stimulation configuration is returned to unipolar in the case of suspected lead failure. The patient notification method of step 650 is no longer necessary since all stimulation will be delivered unipolar at the highest available output in accordance with the high threshold response 300. This stimulation will be perceptible by the patient who will have been advised, under such circumstances, to immediately seek medical attention.

If the lead surveillance method 650 does not measure an abnormal result as determined at decision step 655, the lead failure is assumed not to be the cause of the threshold rise and the bipolar high-energy output is maintained at step 660 in accordance with the high threshold response method 300 (FIG. 4), and patient notification continues according to method 400 (FIG. 5).

Thus, a cardiac stimulation device possessing automatic capture capabilities with a safe and appropriate high threshold response has been presented. This high threshold response that includes a patient notification method improves t-he safety and performance of the cardiac stimulation device by ensuring effective delivery of stimulation therapy under changing threshold conditions and alerts the patient and clinician to a high threshold condition that warrants medical evaluation. These methods have been implemented without requiring additional hardware or complex software. The specific embodiments described herein are intended to illustrate the practice of the invention and are not intended to be limiting the scope of the following claims.

For example, in some situations, reversion to a bipolar output configuration could adversely affect the patient. One such situation involves a primary mechanical failure of the pacing lead, such as when an open circuit occurs due to a fracture of the proximal conductor, or an internal insulation fails. In either situation, the system will read non-capture but unipolar capture may actually be intact. Programming to the bipolar output configuration will result in an effective no output state. Hence, when lead surveillance could be implemented by an algorithm where the system automatically monitors the lead integrity by measuring, for example, stimulation impedance, and obtains a very high (i.e., open circuit), or very low reading (i.e., internal insulation failure), then the automatic capture feature, rather than reverting to a bipolar configuration, effectively disengages, and the stimulation output is set to a predetermined setting, such as 4.5 Volts, which is likely to be adequate with periodic 7.5 Volts unipolar output pulses.

What is claimed:

1. A method of responding to an increase in a capture threshold, for use in a cardiac stimulation device having an automatic capture verification feature, comprising:
   detecting a significant increase in the capture threshold;
   in response to the detecting step, adjusting a stimulation output to a level above the capture threshold;
   in further response to the detecting step, adjusting a stimulation electrode configuration during high output stimulation; and
   delivering a notification to the patient regarding the adjustment of the stimulation output.

2. The method of claim 1, wherein the step of detecting a significant increase in the capture threshold includes detecting a predefined number of consecutive threshold test results that exceed a predefined maximum automatic capture output.

3. The method of claim 2, wherein the step of detecting a significant increase in the capture threshold is programmable.

4. The method of claim 1, wherein the step of adjusting the stimulation output includes setting the stimulation output to a highest output available when the significant increase in the capture threshold is detected.

5. The method of claim 1, wherein the step of adjusting the stimulation output includes setting the stimulation output to a highest pulse amplitude available.

6. The method of claim 1, wherein the step of adjusting the stimulation output includes setting the stimulation output to a highest pulse width available.

7. The method of claim 1 wherein the step of adjusting the stimulation output includes increasing the stimulation output gradually to output settings that are greater than a predetermined maximum automatic capture output.

8. The method of claim 7, wherein the step of detecting a predefined number of consecutive threshold test results includes repeating a plurality of threshold tests on a periodic basis.

9. The method of claim 1, further including the step of switching the stimulation electrode configuration to bipolar stimulation during high output stimulation.

10. The method of claim 9, further including the step of disabling the automatic capture verification feature during bipolar stimulation.

11. The method of claim 9, further including the step of enabling the automatic capture verification feature during high output stimulation.

12. The method of claim 1, wherein the step of delivering the notification includes generating a high output unipolar stimulation pulse.

13. The method of claim 1, wherein the step of delivering the notification includes delivering the notification at a scheduled time.

14. The method of claim 13, wherein the step of delivering the notification includes programming the delivery of the notification.

15. The method of claim 13, wherein the step of delivering the notification includes the step of periodically switching the stimulation electrode configuration from bipolar stimulation to a unipolar stimulation for a predefined number of cardiac cycles.

16. The method of claim 15, wherein the step of periodically switching the stimulation electrode configuration includes effecting a switch for a predefined number of cardiac cycles.

17. The method of claim 16, wherein the step of effecting the switch including effecting the switch for a programmable number of cardiac cycles.

18. The method of claim 1, wherein the step of delivering the notification includes the step of delivering the notification after a predefined number of stimulation cycles.

19. The method of claim 18, wherein the step of delivering the notification includes the step of delivering the notification after a programmable number of stimulation cycles.

20. The method of claim 18, wherein the step of switching the stimulation electrode configuration includes the stimulation electrode configuration from bipolar to unipolar for a predefined number of cardiac cycles following a predetermined number of stimulation cycles.

21. A method of responding to an increase in a capture threshold, for use in a cardiac stimulation device having an automatic capture verification feature, comprising the steps of:
    storing a plurality of capture threshold ranges;
    storing a working margin associated with each capture threshold range;
    measuring a capture threshold;
    categorizing a measured capture threshold in one of the plurality of capture threshold ranges;
    automatically adjusting a stimulation output to the measured capture threshold plus a safety margin associated with the capture threshold range;
    switching to bipolar stimulation if an adjusted stimulation output exceeds a predefined maximum automatic capture output; and
    delivering a notification when the adjusted stimulation output exceeds a predefined alarm level.

22. The method of claim 21, wherein the step of storing the working margin includes storing programmable capture threshold ranges as programmable values.

23. The method of claim 21, wherein the step of delivering the notification includes delivering one or more unipolar stimulation pulses on a scheduled basis.

24. The method of claim 21, wherein the step of delivering the notification includes delivering one or more unipolar stimulation pulses on an event-triggered basis.

25. A method of responding to an increase in a capture threshold, for use in a cardiac stimulation device having an automatic capture verification feature, comprising:
    detecting a significant increase in the capture threshold;
    adjusting a stimulation output to a level above the capture threshold;
    v us adjusting a stimulation electrode configuration during high output stimulation;
    delivering a notification to the patient about a change in the stimulation output;
    checking one or more stimulation leads for evidence of lead failure; and
    adjusting the stimulation electrode configuration if lead failure is detected.

26. The method of claim 25, wherein the step of checking one or more stimulation leads for evidence of lead failure includes performing lead impedance measurements.

27. The method of claim 25, further including the step of switching the stimulation electrode configuration to a unipolar configuration if lead failure is detected.

28. A cardiac stimulation device capable of implementing automatic capture verification, for responding to an increase in a capture threshold, comprising:
    a pulse generator that selectively generates stimulation pulses;
    a lead connected to the pulse generator, that delivers the stimulation pulses to one or more cardiac chambers;
    a sensing circuit connected to the lead that detects the occurrence of a significant increase in the capture threshold;
    a control circuit that responds to the significant increase in the capture threshold by adjusting a stimulation output to a level above the capture threshold and by further adjusting a stimulation electrode configuration during high output stimulation; and
    notification circuit that delivers a notification to the patient regarding the adjustment of the stimulation output.

29. The device of claim 28, wherein the significant increase in capture threshold is detected by a predefined number of consecutive threshold test results that exceed a maximum output defined for automatic capture.

30. The device of claim 29, wherein the number of consecutive threshold test results required for detection of the large increase in capture threshold is programmable.

31. The device of claim 30, wherein the stimulation output is set to a highest output available when the significant increase in capture threshold is detected.

32. The device of claim 28, wherein the stimulation output is set to a highest pulse amplitude available.

33. The device of claim 28, wherein the stimulation output is set to a highest pulse width available.

34. The device of claim 28, wherein the stimulation output is increased stepwise to output settings greater than a maximum output defined for automatic capture.

35. The device of claim 28, wherein the electrode configuration is switched to a bipolar configuration during high output stimulation.

36. A cardiac stimulation device capable of implementing automatic capture verification, for responding to an increase in a capture threshold, comprising:
    a pulse generator that selectively generates stimulation pulses;
    a lead connected to the pulse generator, that delivers the stimulation pulses to one or more cardiac chambers;
    a sensing circuit connected to the lead that detects the occurrence of a significant increase in the capture threshold, and that measures a capture threshold;
    memory for storing a plurality of capture threshold ranges and a working margin associated with each capture threshold range;
    a control circuit connected to the sensing circuit and the memory, that categorizes a measured capture threshold in one of the plurality of capture threshold ranges and that automatically adjusts a stimulation output to the measured capture threshold plus a safety margin associated with the capture threshold range; and
    a switch connected to the control circuit that switches to bipolar stimulation if an adjusted stimulation output exceeds a predefined maximum automatic capture output.

37. The device of claim 36, further including a notification module that generates an alarm when the adjusted stimulation output exceeds a predefined alarm level.

38. The device of claim 37, wherein the plurality of capture threshold ranges include programmable values.

39. The device of claim 37, wherein the working margin associated with each capture threshold range is a programmable value.

40. The device of claim 37, wherein the notification module delivers one or more unipolar stimulation pulses on a scheduled basis.

41. A cardiac stimulation device capable of implementing automatic capture verification, for responding to an increase In a capture threshold, comprising:

means for detecting a significant increase in the capture threshold;

means for adjusting a stimulation output to a level above the capture threshold in response to the significant increase in the capture threshold;

means for adjusting a stimulation electrode configuration during a high stimulation output in further response to the significant increase in the capture threshold; and means for notifying the patient regarding the adjustment of the stimulation output.

42. The device of claim 41, wherein the significant increase in capture threshold is detected by a predefined number of consecutive threshold test results that exceed a maximum output defined for automatic capture.

43. The device of claim 42, wherein the number of consecutive threshold test results required for detection of the large increase in capture threshold is programmable.

44. The device of claim 42, wherein the stimulation output is set to a highest output available when the significant increase in capture threshold is detected.

45. The device of claim 41, wherein the stimulation output is set to any one of the following:

a highest pulse amplitude available; or a highest pulse width available.

46. The device of claim 41, wherein the stimulation electrode configuration is switched to a bipolar configuration during high output stimulation.

47. The device of claim 41, wherein the stimulation output is set to a highest level available and, when applicable, stimulation is switched to, and is maintained in a unipolar output configuration.

48. The device of claim 41, wherein the stimulation output is set to a highest level available; and when applicable, stimulation is switched to, and is maintained in a unipolar output configuration, wherein the stimulation output is insufficient to evoke local muscle stimulation and wherein the means for delivering the notification is programmable to an output level that is greater than the highest level.

49. The device in claim 48, further including means for delivering periodic notification signals.

* * * * *